United States Patent
Abbondanza et al.

(10) Patent No.: US 11,706,979 B2
(45) Date of Patent: Jul. 18, 2023

(54) DISUBSTITUTED DIARYLOXYBENZOHETERODIAZOLE COMPOUNDS

(71) Applicant: ENI S.P.A., Rome (IT)

(72) Inventors: Luigi Abbondanza, Novara (IT); Andrea Alessi, Novara (IT); Antonio Alfonso Proto, Novara (IT); Giuliana Schimperna, Novara (IT); Liliana Gila, Casalino (IT)

(73) Assignee: Eni S.P.A., Rome (IT)

( * ) Notice: Subject to any disclaimer, the term of this patent is extended or adjusted under 35 U.S.C. 154(b) by 51 days.

(21) Appl. No.: 17/380,967

(22) Filed: Jul. 20, 2021

(65) Prior Publication Data

US 2021/0408393 A1 Dec. 30, 2021

Related U.S. Application Data

(62) Division of application No. 15/514,412, filed as application No. PCT/EP2015/071987 on Sep. 24, 2015, now Pat. No. 11,133,474.

(30) Foreign Application Priority Data

Sep. 25, 2014 (IT) .......................... MT2014A001663
May 27, 2015 (IT) ......................... 102015000018310

(51) Int. Cl.
*H10K 85/60* (2023.01)
*C07D 417/14* (2006.01)
(Continued)

(52) U.S. Cl.
CPC .......... *H10K 85/657* (2023.02); *C07D 417/14* (2013.01); *C09K 11/02* (2013.01);
(Continued)

(58) Field of Classification Search
CPC ...... C07D 417/14; C09K 11/06; C09K 11/02; C09K 2211/1011; C09K 2211/1007;
(Continued)

(56) References Cited

U.S. PATENT DOCUMENTS

| | | | | |
|---|---|---|---|---|
| 2006/0052612 A1* | 3/2006 | Stossel | ................ | C07D 285/14 548/134 |
| 2008/0093985 A1* | 4/2008 | Morishita | .............. | H05B 33/14 257/E51.026 |
| 2015/0291575 A1* | 10/2015 | Santarelli | ............. | C07D 285/14 548/126 |

FOREIGN PATENT DOCUMENTS

| | | | | |
|---|---|---|---|---|
| EP | 2557606 A1 | 2/2013 | | |
| EP | 2730600 A1 * | 5/2014 | .......... | C08G 61/123 |

(Continued)

OTHER PUBLICATIONS

Kulartne R.S. et al., Journal of Materials Chemistry A (2013), pp. 15535-15543, vol. 1(48).

(Continued)

*Primary Examiner* — Michael Y Sun
(74) *Attorney, Agent, or Firm* — Praedcere Law

(57) ABSTRACT

Disubstituted diaryloxybenzoheterodiazole compound of general formula (I):

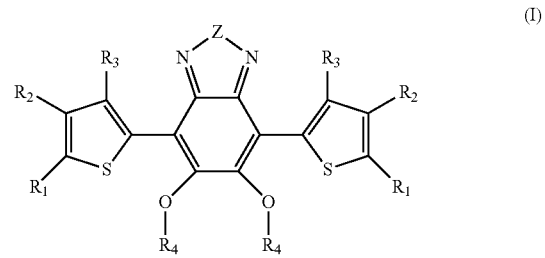

in which:
Z represents a sulfur atom, an oxygen atom, a selenium atom; or an $NR_5$ group in which $R_5$ is selected from linear or branched $C_1$-$C_{20}$, or from optionally substituted aryl groups;
$R_1$, $R_2$, $R_3$ and $R_4$ are as defined in the claims. The disubstituted diaryloxybenzoheterodiazole compound of general formula (I) can advantageously be used as a (Continued)

spectrum converter in luminescent solar concentrators (LSCs) which are in turn capable of improving the performance of photovoltaic devices (or solar devices) selected, for example, from photovoltaic cells (or solar cells), photovoltaic modules (or solar modules) on either a rigid substrate or a flexible substrate.

5 Claims, 2 Drawing Sheets

(51) Int. Cl.
| | | |
|---|---|---|
| *C09K 11/06* | (2006.01) | |
| *H02S 40/22* | (2014.01) | |
| *H10K 30/87* | (2023.01) | |
| *H10K 30/00* | (2023.01) | |
| *H10K 39/10* | (2023.01) | |
| *H10K 85/10* | (2023.01) | |
| *C09K 11/02* | (2006.01) | |
| *H01L 31/0232* | (2014.01) | |
| *H01L 27/146* | (2006.01) | |

(52) U.S. Cl.
CPC ............... *C09K 11/06* (2013.01); *H02S 40/22* (2014.12); *H10K 30/451* (2023.02); *H10K 30/87* (2023.02); *H10K 39/10* (2023.02); *H10K 85/141* (2023.02); *H10K 85/626* (2023.02); *H10K 85/655* (2023.02); *C09K 2211/1007* (2013.01); *C09K 2211/1011* (2013.01); *C09K 2211/1051* (2013.01); *C09K 2211/1092* (2013.01); *H01L 27/14663* (2013.01); *H01L 31/02322* (2013.01); *Y02E 10/52* (2013.01)

(58) Field of Classification Search
CPC .... C09K 2211/1051; C09K 2211/1092; H01L 31/055; H01L 51/0058; H01L 51/0071; H01L 51/447; H01L 31/02322; H01L 51/0068; H01L 27/301; H01L 51/004; H01L 27/14663; H01L 51/4206; H02S 40/22; Y02E 10/549; Y02E 10/52
See application file for complete search history.

(56) References Cited

FOREIGN PATENT DOCUMENTS

| | | | | |
|---|---|---|---|---|
| EP | 2730600 A1 | 5/2014 | | |
| WO | WO2011048458 A1 | 4/2011 | | |
| WO | WO-2012007834 A1 * | 1/2012 | ........... | C07D 285/14 |
| WO | WO2012007834 A1 | 1/2012 | | |

OTHER PUBLICATIONS

Wang N. et al., Journal of the American Chemical Society (2013), pp. 17060-17068, vol. 135(45).
Zhou H. et al., Angewandte Chemie International Edition (2011), p. 2995-2998, vol. 50(13).
Velusamy M. et al., "Organic dyes incorporating low-band gap chromophores for dye-sensitized solar cells," Organic Letters, American Chemical Society (2005), pp. 1899-1902, vol. 7(10).
Kono et al., "High-performance and light-emitting n-type organic field effect transistors based on dithienylbenzothiadiazole and related heterocycles," Chemistry of Materials, American Chemical Society (2007), pp. 1218-1220, vol. 19(6).
International Search Report and Written Opinion for PCT/EP2015/071987, dated Nov. 16, 2015, 12 pages.

* cited by examiner

DISUBSTITUTED DIARYLOXYBENZOHETERODIAZOLE COMPOUNDS

The present invention relates to a disubstituted diaryloxybenzoheterodiazole compound.

More particularly, the present invention relates to a diaryloxybenzoheterodiazole compound disubstituted with thiophenyl groups.

The present invention also relates to processes for the preparation of the said diaryloxybenzoheterodiazole compound disubstituted with thiophenyl groups.

The said diaryloxybenzoheterodiazole compound disubstituted with thiophenyl groups can advantageously be used as a spectrum converter in luminescent solar concentrators (LSCs) which are in turn capable of improving the performance of photovoltaic devices (or solar devices) selected, for example, from photovoltaic cells (or solar cells), photovoltaic modules (or solar modules) on either a rigid substrate or a flexible substrate.

The present invention also relates to a luminescent solar concentrator (LSC) including at least one diaryloxybenzoheterodiazole compound disubstituted with thiophenyl groups as a photovoltaic device (or solar device) comprising the said luminescent solar concentrator (LSC).

In the state of the art, one of the main limitations on utilization of the energy of solar radiations is the ability of photovoltaic devices (or solar devices) to absorb optimally only radiations having wavelengths falling within a narrow spectral range.

In comparison with the spectral range of solar radiation which extends from wavelengths of approximately 300 nm to wavelengths of approximately 2500 nm, photovoltaic cells (or solar cells) based on crystalline silicon, for example, have an optimum absorption zone (effective spectrum) in the range 900 nm-1100 nm, while polymer photovoltaic cells (or solar cells) are likely to become damaged if exposed to radiations having a wavelength less than approximately 500 nm because of the photodegradation phenomena caused, which become significant below that limit. Typically, the efficiency of photovoltaic devices (or solar devices) according to the state of the art is a maximum in the spectral region ranging from 570 nm to 680 nm (yellow-orange).

The abovementioned disadvantages bring about limited external quantum efficiency (EQE) in photovoltaic devices (or solar devices), defined as the ratio between the number of electron-hole pairs generated in the semiconductor material of photovoltaic devices (or solar devices) and the number of photons incident on the said photovoltaic devices (or solar devices).

A number of devices placed between the light radiation source (the sun) and the photovoltaic devices (or solar devices) have been developed to improve the external quantum efficiency (EQE) of photovoltaic devices (or solar devices); these selectively absorb incident radiation having wavelengths outside the effective spectrum of the said photovoltaic devices (or solar devices), emitting the absorbed energy in the form of photons having a wavelength falling within the effective spectrum. Said devices are known as luminescent solar concentrators (LSCs). When the energy of the photons re-emitted from the luminescent solar concentrators (LSCs) is higher than that of the incident photons, the process of photoluminescence, comprising absorption of the solar radiation and subsequent re-emission of photons having a shorter wavelength, is also known as the "up-conversion" process. Conversely, when the energy of the photons emitted by the luminescent solar concentrators (LSCs) is lower than that of the incident photons, the photoluminescent process is defined as a "down-conversion" (or "down-shifting") process.

Generally, the said luminescent solar concentrators (LSCs) comprise large sheets of a material which is transparent to solar radiation (for example, polymer or inorganic glasses) within which fluorescent compounds acting as spectrum converters are dispersed or chemically bonded to said material. As a result of the effect of the optical phenomenon of total reflection the radiation emitted by the fluorescent compounds is "guided" towards the thin edges of the sheet where it is concentrated on photovoltaic cells (or solar cells) located there. In this way, extensive surface areas of low cost material (the photoluminescent sheets) can be used to concentrate light onto the small surface areas of high cost materials [photovoltaic cells (or solar cells)].

The fluorescent compounds can be deposited on the glass substrate in the form of thin film or, as in the case of polymer materials, they can be dispersed within the polymer matrix. Alternatively, the polymer matrix can be directly functionalized with fluorescent chromophor groups.

Ideally, for use in spectrum converters, fluorescent compounds must have the following properties:

a high luminescence quantum efficiency ($\Phi$) [($\Phi$) is defined according to equation (1) shown below as the ratio between the number of photons emitted and the number of photons adsorbed by a luminescent molecule per unit time, and has a maximum value of 1:

($\Phi$)=number of photons emitted/number of photons absorbed (1);

a wide absorption band in the spectral region within which the photovoltaic device (or solar device) is not very efficient;

a high absorption coefficient;

a narrow emission band in the spectral region in which the photovoltaic device (or solar device) is mostly efficient;

well-separated absorption and emission bands to prevent or minimize auto absorption phenomena.

It is known that some benzothiadiazole compounds, in particular 4,7-di-(thien-2'-yl)-2,1,3-benzothiadiazole (DTB), are fluorescent compounds which can be used in the construction of luminescent solar concentrators (LSCs). Compounds of this type have been described in International Patent Application WO 2011/048458 in the name of the Applicant.

4,7-di-(thien-2'-yl)-2,1,3-benzothiadiazole (DTB) is characterized by emission centred around 579 nm, a value corresponding to an energy well above the minimum functioning threshold of photovoltaic cells (or solar cells), a threshold which, for example, corresponds to a wavelength of around 1100 nm in the case of the most widely used photovoltaic cells (or solar cells) based on silicon. In addition, its light radiation absorption is intense and extensive over a relatively wide range of wavelengths, ranging indicatively from 550 nm (the wavelength of green radiation) to the ultraviolet. Finally, 4,7-di-(thien-2'-yl)-2,1,3-benzothiadiazole (DTB) has a Stokes shift in dichloromethane solution of 134 nm, which is very much higher than that of most commercial products hitherto proposed for use in luminescent solar concentrators (LSCs).

For these reasons, the use of 4,7-di-(thien-2'-yl)-2,1,3-benzothiadiazole (DTB) has made it possible to construct luminescent solar concentrators (LSCs) of excellent quality. Although absorbing a significant part of the solar spectrum, 4,7-di-(thien-2'-yl)-2,1,3-benzothiadiazole (DTB) nevertheless has modest absorption in regions of greater wavelength, corresponding to yellow and red radiations, which cannot therefore be converted into others which can be more effectively utilized by a photovoltaic cell (or solar cell).

The Applicant has therefore set itself the problem of finding fluorescent compounds which are capable of providing performances which are comparable to or even better than those of known benzothiadiazole compounds, in particular in terms of the power generated by the photovoltaic devices in which they are used.

The Applicant has now found that disubstituted diaryloxybenzoheterodiazole compounds having a specific general formula (i.e. of general formula (I) indicated below) can be advantageously used in the construction of luminescent solar concentrators (LSCs). The said luminescent solar concentrators (LSCs) can in turn be advantageously used, for example, together with photovoltaic cells (or solar cells), in the construction of photovoltaic devices (or solar devices). Said disubstituted diaryloxybenzoheterodiazole compounds are capable of providing performances which are comparable to or even better than those of known benzothiadiazole compounds, in particular in terms of the power generated by the photovoltaic devices in which they are used. Moreover, the Applicant has found that said disubstituted diaryloxybenzoheterodiazole compounds have excellent photostability and, therefore, higher durability over time.

Thus an object of the present invention relates to a disubstituted diaryloxybenzoheterodiazole compound of general formula (I):

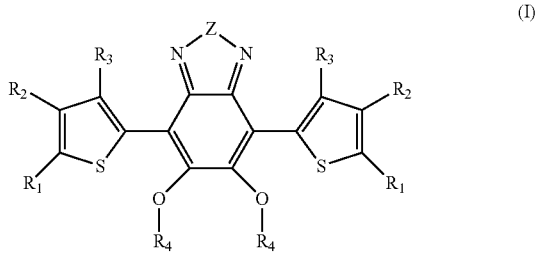

in which:

Z represents a sulfur atom, an oxygen atom, a selenium atom; or an $NR_5$ group in which $R_5$ is selected from linear or branched $C_1$-$C_{20}$, preferably $C_1$-$C_8$, alkyl groups, or from optionally substituted aryl groups;

$R_1$, $R_2$ and $R_3$, which are the same or different, represent a hydrogen atom; or are selected from linear or branched $C_1$-$C_{20}$, preferably $C_1$-$C_8$, alkyl groups, optionally containing heteroatoms, optionally substituted cycloalkyl groups, optionally substituted aryl groups, optionally substituted linear or branched $C_1$-$C_{20}$, preferably $C_1$-$C_8$, alkoxyl groups, optionally substituted phenoxyl groups, or —$OCOR_6$ groups in which $R_6$ is selected from linear or branched $C_1$-$C_{20}$, preferably $C_1$-$C_8$, alkyl groups, or is a cyano group;

or $R_1$ and $R_2$ can optionally be linked together so as to form, together with the carbon atoms to which they are linked, a saturated, unsaturated or aromatic cyclic ring or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;

or $R_2$ and $R_3$ can optionally be linked together so as to form, together with the carbon atoms to which they are linked, a saturated, unsaturated or aromatic cyclic ring or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;

$R_4$, which are the same or different, are selected from optionally substituted aryl groups.

For the purpose of the present description and of the following claims the definitions of numerical intervals always comprise the end numbers unless specified otherwise.

For the purpose of the present description and of the following claims the term "comprising" also includes the terms "which essentially consists of" or "which consists of".

The term "$C_1$-$C_{20}$ alkyl groups" means alkyl groups having from 1 to 20 carbon atoms, linear or branched. Specific examples of $C_1$-$C_{20}$ alkyl groups are: methyl, ethyl, n-propyl, iso-propyl, n-butyl, iso-butyl, t-butyl, pentyl, 2-ethylhexyl, hexyl, heptyl, octyl, nonyl, decyl, dodecyl.

The term "$C_1$-$C_{20}$ alkyl groups optionally containing heteroatoms" means alkyl groups having from 1 to 20 carbon atoms, linear or branched, saturated or unsaturated, in which at least one of the hydrogen atoms is replaced with a heteroatom selected from: halogens such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichlororoethyl, 2,2,3,3-tetrafluoropropyl, 2,2,3,3,3-pentafluoropropyl, perfluoropentyl, perfluoroctyl, perfluorodecyl, oxymethyl, thiomethyl, thioethyl, dimethylamino, propylamino, dioctylamino.

The term "cycloalkyl groups" means cycloalkyl groups having from 3 to 10 carbon atoms. Said cycloalkyl groups can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amine groups; nitro groups; aryl groups. Specific examples of cycloalkyl groups are: cyclopropyl, 1,4-dioxin, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl groups" means aromatic carbocyclic groups. Said aryl groups can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amine groups; nitro groups; aryl groups. Specific examples of aryl groups are: methylphenyl, dimethylphenyl, trimethylphenyl, di-iso-propylphenyl, t-butylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene.

The term "$C_1$-$C_{20}$ alkoxyl groups" means alkoxyl groups having from 1 to 20 carbon atoms, linear or branched. Said alkoxyl groups can be substituted with one or more groups, which are the same or different, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amine groups; nitro groups. Specific examples of $C_1$-$C_{20}$ alkoxyl groups are: methoxyl, ethoxyl, fluoroethoxyl, n-propoxyl, iso-propoxyl, n-butoxyl, n-fluoro-butoxyl, iso-butoxyl, t-butoxyl, pentoxyl, hexyloxyl, heptyloxyl, octyloxyl, nonyloxyl, decyloxyl, dodecyloxyl.

The term "optionally substituted phenoxyl groups" means phenoxyl groups $C_6H_5O$ which can be substituted with one or more groups, which are the same or different, selected from: halogen atoms such as, for example, fluorine, chlorine, preferably fluorine; $C_1$-$C_{20}$ alkyl groups; $C_1$-$C_{20}$ alkoxyl groups; aryl groups; cyano groups; amine groups; nitro groups. Specific examples of phenoxyl groups $C_6H_5O$ are: phenoxyl, 4-nitro-phenoxyl, 2,4-di-nitrophenoxyl, 2-chloro-4-nitrophenoxyl, 2-fluoro-4-nitrophenoxyl, 3-fluoro-4-nitrophenoxyl, 5-fluoro-2-nitrophenoxyl, 2-aminophenoxyl.

In accordance with a preferred embodiment of the present invention, in the said general formula (I):

Z represents a sulfur atom;

$R_1$, which are the same, represent a hydrogen atom; or are selected from optionally substituted aryl groups, preferably are 2,6-dimethylphenyl, 2,5-dimethylphenyl, 2,6-di-iso-propylphenyl, naphthyl;

$R_2$ and $R_3$, which are the same, represent a hydrogen atom;

$R_4$, which are the same, are selected from optionally substituted aryl groups, preferably are phenyl, t-butylphenyl, naphthyl, 2,6-dimethylphenyl, diphenyl.

Specific examples of compounds of general formula (I) which are useful for the purpose of the present invention are shown in Table 1.

TABLE 1

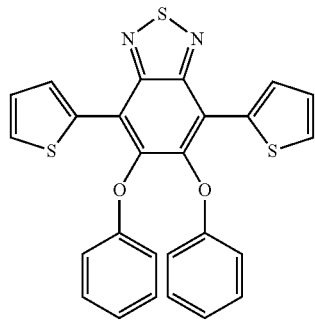 [SMILES: c1ccc(Oc2c(Oc3ccccc3)c(-c3cccs3)c3nsnc3c2-c2cccs2)cc1]
(Ia)

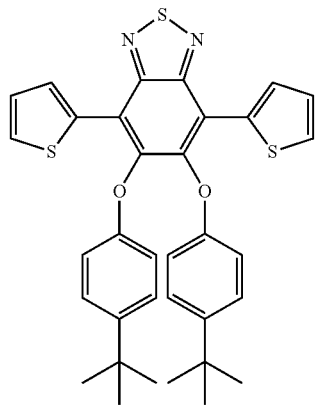 [SMILES: CC(C)(C)c1ccc(Oc2c(Oc3ccc(C(C)(C)C)cc3)c(-c3cccs3)c3nsnc3c2-c2cccs2)cc1]
(Ib)

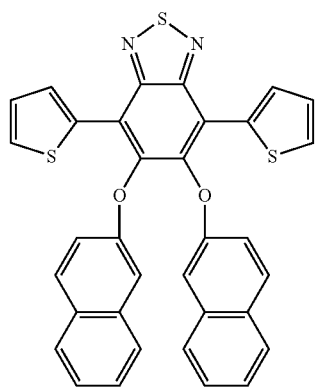 [SMILES: c1csc(-c2c(Oc3ccc4ccccc4c3)c(Oc3ccc4ccccc4c3)c(-c3cccs3)c3nsnc23)c1]
(Ic)

TABLE 1-continued
| | |
|---|---|
| 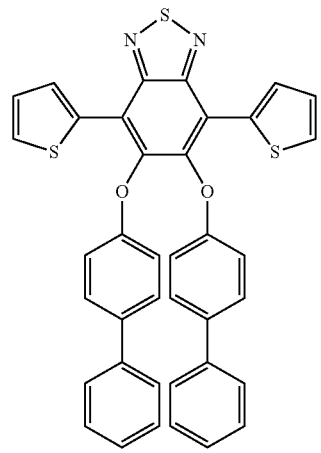 [SMILES: c1ccc(-c2ccc(Oc3c(Oc4ccc(-c5ccccc5)cc4)c(-c4cccs4)c4nsnc4c3-c3cccs3)cc2)cc1] | (Id) |
| 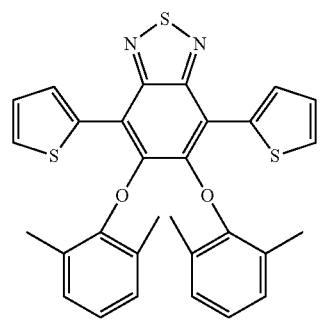 [SMILES: Cc1cccc(C)c1Oc1c(Oc2c(C)cccc2C)c(-c2cccs2)c2nsnc2c1-c1cccs1] | (Ie) |
| 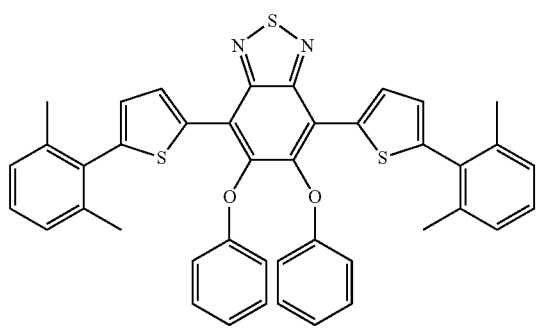 [SMILES: Cc1cccc(C)c1-c1ccc(-c2c(Oc3ccccc3)c(Oc3ccccc3)c(-c3ccc(-c4c(C)cccc4C)s3)c3nsnc23)s1] | (If) |
| 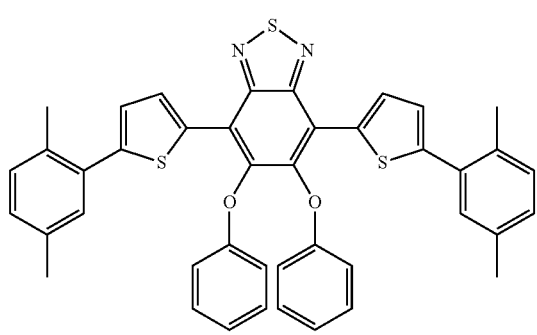 [SMILES: Cc1ccc(C)c(-c2ccc(-c3c(Oc4ccccc4)c(Oc4ccccc4)c(-c4ccc(-c5cc(C)ccc5C)s4)c4nsnc34)s2)c1] | (Ig) |

TABLE 1-continued

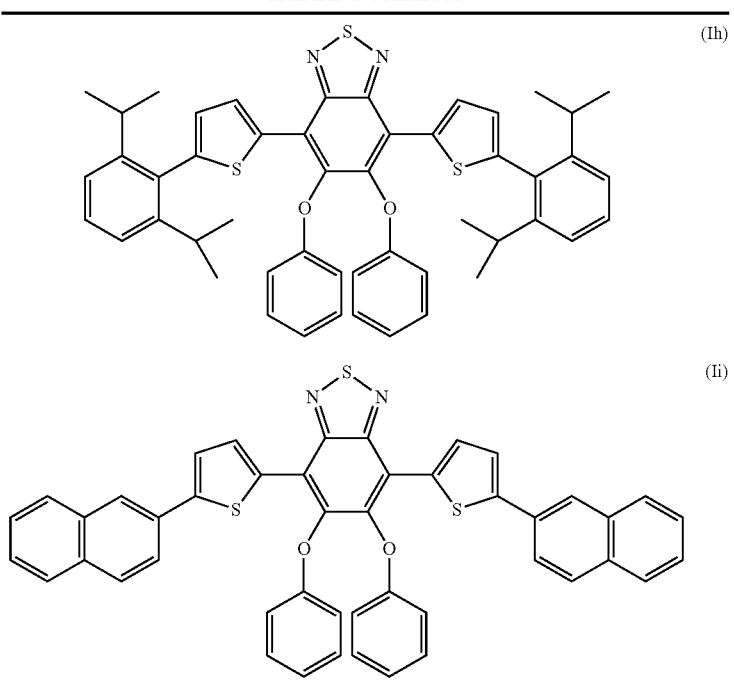

(Ih)

(Ii)

The present invention also relates to processes for preparing the disubstituted diaryloxybenzoheterodiazole compound of general formula (I).

A further object of the present invention is therefore a first process for the preparation of a disubstituted diaryloxybenzoheterodiazole compound of general formula (I):

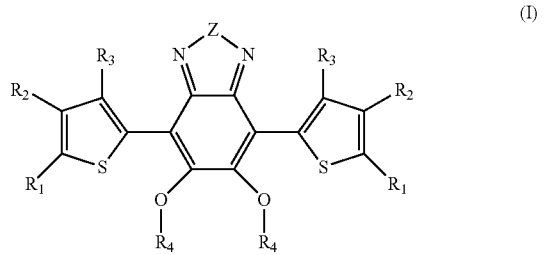

(I)

in which Z has the same meanings as described above, $R_1$, which are the same, represent a hydrogen atom, $R_2$ and $R_3$, have the same meanings as described above, preferably represent a hydrogen atom, comprising reacting at least one fluorinated disubstituted benzoheterodiazole compound of general formula (II):

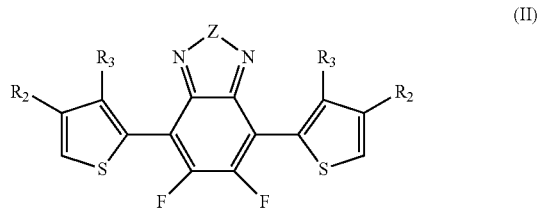

(II)

in which Z has the same meanings as described above, $R_2$ and $R_3$ have the same meanings as described above, preferably represent a hydrogen atom, with at least one aryl alcohol of general formula (III):

$$R_4\text{—OH} \qquad (III)$$

in which $R_4$ has the same meanings as described above.

In accordance with a preferred embodiment of the present invention, the said fluorinated disubstituted benzoheterodiazole compound of general formula (II) and the said aryl alcohol of general formula (III) can be used in molar ratios ranging from 1:2 to 1:10, preferably ranging from 1:2 to 1:5.

In accordance with a preferred embodiment of the present invention the said process can be carried out in the presence of at least one weak organic base which can be selected, for example, from: alkali metal (e.g., sodium, potassium, caesium) or alkaline-earth metal (e.g., magnesium, calcium) carboxylates such as, for example, potassium acetate, sodium acetate, caesium acetate, magnesium acetate, calcium acetate, potassium propionate, sodium propionate, caesium propionate, magnesium propionate, calcium propionate, or their mixtures; alkali metal (e.g., lithium, sodium, potassium, caesium) or alkaline-earth metal (e.g., magnesium, calcium) carbonates such as, for example, lithium carbonate, potassium carbonate, sodium carbonate, caesium carbonate, magnesium carbonate, calcium carbonate, or their mixtures; alkali metal (e.g., lithium, sodium, potassium, caesium) or alkaline-earth metal (e.g., magnesium, calcium) bicarbonates such as, for example, lithium bicarbonate, potassium bicarbonate, sodium bicarbonate, caesium bicarbonate, magnesium bicarbonate, calcium bicarbonate, or their mixtures; preferably potassium carbonate, sodium carbonate, caesium carbonate. Preferably, the said fluorinated disubstituted benzoheterodiazole compound of general formula (II) and the said weak organic base can be used in molar ratios ranging from 1:1 to 1:10, preferably ranging from 1:2 to 1:5.

In accordance with a preferred embodiment of the present invention, the said process can be carried out in the presence of at least one organic solvent which can be selected, for example, from: ethers such as, for example, 1,2-dimethoxyethane, 1,4-dioxane, tetrahydrofuran, or their mixtures; hydrocarbons such as, for example, toluene, xylene, or their mixtures; dipolar aprotic solvents such as, for example, N,N-dimethylformamide, N-methylpyrrolidone, dimethylsulfoxide, or their mixtures; preferably N,N-dimethylformamide.

In accordance with a preferred embodiment of the present invention the said fluorinated disubstituted benzoheterodiazole compound of general formula (II) can be used in the said organic solvent in quantities such as to have a molar concentration in the said organic solvent ranging from 0.05 M to 2 M, preferably ranging from 0.1 M to 1 M. In accordance with a preferred embodiment of the present invention the said process can be carried out at a temperature ranging from 60° C. to 150° C., preferably ranging from 80° C. to 100° C.

In accordance with a preferred embodiment of the present invention, the said process can be carried out in a time ranging from 1 hour to 24 hours, preferably ranging from 2 hours to 12 hours.

Generally, distilled water is added to the mixture obtained at the end of the said process, obtaining a precipitate which is recovered by filtration. Subsequently, in the case in which an alcohol which is highly soluble in water such as, for example, phenol, is used, the precipitate obtained is purified merely by washing with distilled water. Conversely, in the case in which an alcohol which is not highly soluble in water, such as, for example, substituted phenol, is used, the precipitate obtained is purified by normal methods of purification such as, for example, elution in a silica gel chromatography column and/or crystallisation from organic solvents such as, for example: hydrocarbons (e.g., n-heptane, hexane, toluene, or their mixtures); chlorinated solvents (e.g., dichloromethane, chloroform, or their mixtures); ester solvents (e.g., ethyl acetate, methyl acetate, methyl propionate, or their mixtures); ether solvents (e.g., ethyl ether, tetrahydrofuran, t-butylmethylether, or their mixtures); alcohols (e.g., methanol, ethanol, propanol, or their mixtures); or their mixtures.

A further object of the present invention is also a second process for the preparation of a disubstituted diaryloxybenzoheterodiazole compound of general formula (I):

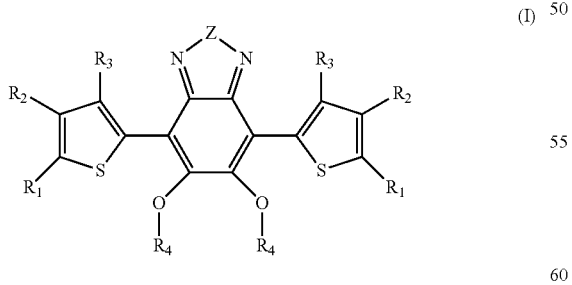

in which Z has the same meanings as described above, $R_1$, $R_2$ and $R_3$, are the same or different and at least one of $R_1$, $R_2$ and $R_3$, preferably at least two, more preferably the two $R_1$ substituents are not hydrogen, comprising the following steps:

(a) reacting at least one disubstituted diaryloxybenzoheterodiazole compound of general formula (Ia1):

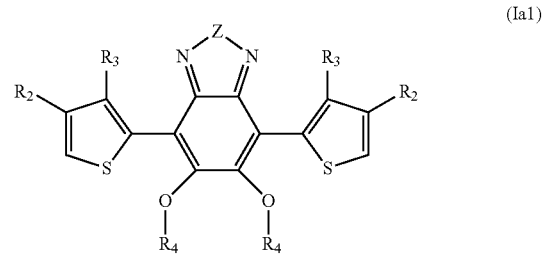

in which Z, $R_2$, $R_3$ and $R_4$, have the same meanings as described above, preferably $R_2$ and $R_3$ represent a hydrogen atom, with at least one compound selected from N-haloimides such as, for example, N-bromosuccinimide, N-bromophthalimide, N-iodosuccinimide, N-iodophthalimide, obtaining a halogenated disubstituted diaryloxybenzoheterodiazole compound of general formula (IV):

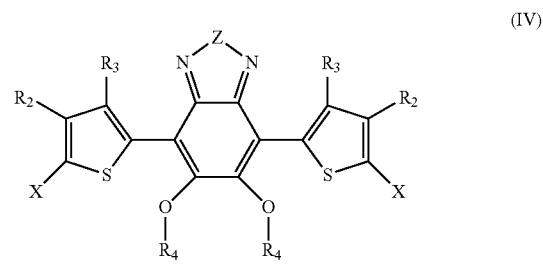

in which Z, $R_2$, $R_3$ and $R_4$, have the same meanings as described above, preferably $R_2$ and $R_3$ represent a hydrogen atom, and X is a halogen atom selected from bromine, iodine, preferably bromine;

(b) reacting the halogenated disubstituted diaryloxybenzoheterodiazole compound of general formula (IV) obtained in step (a) with:

(i) at least one aryl-boron compound of general formula (V):

in which $R_1$ has the same meanings as described above provided that the $R_1$ substituent does not represent a hydrogen atom, and $R_7$ the substituents represent a hydrogen atom, or can be selected from linear or branched $C_1$-$C_{10}$ alkyl groups, or optionally substituted cycloalkyl groups, or the two $R_7$ substituents can optionally be linked together so as to form, together with the other atoms to which they are linked, a cyclic ring as in the case of the pinacol esters of boronic acid or of the 1,3-propanodiol esters of boronic acid; or (ii) with at least one aryl-stannylated compound of general formula (VI):

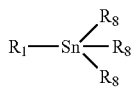

(VI)

in which $R_1$ has the same meanings as described above provided that the $R_1$ substituent does not represent a hydrogen atom, and the $R_8$ substituents can be selected from linear or branched $C_1$-$C_8$ alkyl groups;

preferably with at least one aryl-boron compound of general formula (V).

In accordance with a preferred embodiment of the present invention, in the said step (a) the said disubstituted diaryloxybenzoheterodiazole compound of general formula (Ia1) and the said compound selected from N-haloimides can be used in molar ratios ranging from 1:2 to 1:3, preferably ranging from 1:2 to 1:2.5.

In accordance with a preferred embodiment of the present invention the said step (a) can be carried out in the presence of at least one organic solvent which can be selected, for example, from: ethers such as, for example, 1,2-dimethoxyethane, 1,4-dioxane, tetrahydrofuran, or their mixtures; chlorinated solvents such as, for example, dichloromethane, chloroform, or their mixtures; dipolar aprotic solvents such as, for example, N,N-dimethylformamide, N-methylpyrrolidone, dimethylsulfoxide; or their mixtures; preferably tetrahydrofuran.

In accordance with a preferred embodiment of the present invention the said disubstituted diaryloxybenzoheterodiazole compound of general formula (Ia1) can be used in the said organic solvent in quantities such as to have a molar concentration in the said organic solvent ranging from 0.01 M to 5 M, preferably ranging from 0.1 M to 2 M. In accordance with a preferred embodiment of the present invention the said step (a) can be carried out at a temperature ranging from 20° C. to 50° C., preferably ranging from 20° C. to 30° C.

In accordance with a preferred embodiment of the present invention the said step (a) can be carried out in a time ranging from 1 hour to 24 hours, preferably ranging from 4 hours to 18 hours.

Generally, at the end of the said step (a) the mixture obtained, after the addition of distilled water, is filtered obtaining a residue which is washed with distilled water in order to wholly remove the N-imide which forms during the reaction and the product obtained can be used as such in step (b).

For the purpose of the present invention the said step (b) can be carried out in accordance with the Suzuki reaction.

In accordance with one embodiment of the present invention, in the said step (b) the said disubstituted halogenated diaryloxybenzoheterodiazole compound of general formula (IV) and the said aryl-boron compound of general formula (V), or the said arylstannylate compound of general formula (VI), can be used in molar ratios ranging from 1:2 to 1:5, preferably ranging from 1:2 to 1:4.

In accordance with a preferred embodiment of the present invention, the said step (b) can be carried out in the presence of at least one catalyst containing palladium which can be selected from compounds of palladium in oxidation state (0) or (II) such as, for example, palladium-tetrakistriphenylphosphine [Pd(PPh$_3$)$_4$], bis-triphenylphosphine palladium dichloride [PdCl$_2$(PPh$_3$)$_2$]. Preferably, the said disubstituted halogenated diaryloxybenzoheterodiazole compound of general formula (IV) and the said catalyst can be used in molar ratios ranging from 1:0.15 to 1:0.01, preferably ranging from 1:0.02 to 1:0.12.

In accordance with a preferred embodiment of the present invention the said step (b) can be carried out in the presence of at least one weak organic base which can be selected, for example, from: alkali metal (e.g., sodium, potassium, caesium) or alkaline-earth metal (e.g., magnesium, calcium) carboxylates such as, for example, potassium acetate, sodium acetate, caesium acetate, magnesium acetate, calcium acetate, potassium propionate, sodium propionate, caesium propionate, magnesium propionate, calcium propionate, or their mixtures; alkali metal (e.g., lithium, sodium, potassium, caesium) or alkaline-earth metal (e.g., magnesium, calcium) carbonates such as, for example, lithium carbonate, potassium carbonate, sodium carbonate, caesium carbonate, magnesium carbonate, calcium carbonate, or their mixtures; alkali metal (e.g., lithium, sodium, potassium, caesium) or alkaline-earth metal bicarbonates (e.g., magnesium, calcium) such as, for example, lithium bicarbonate, potassium bicarbon bicarbonate, sodium bicarbonate, caesium bicarbonate, magnesium bicarbonate, calcium bicarbonate, or their mixtures; preferably potassium carbonate, sodium carbonate, caesium carbonate. In the said step (b), the said base can be used as such, or in aqueous solution. Preferably, the said disubstituted halogenated diaryloxybenzoheterodiazole compound of general formula (IV) and the said weak organic base can be used in molar ratios ranging from 1:1 to 1:20, preferably ranging from 1:2 to 1:10.

In accordance with a preferred embodiment of the present invention the said step (b) can be carried out in the presence of at least one organic solvent which can be selected, for example, from: ethers such as, for example, 1,2-dimethoxyethane, 1,4-dioxane, tetrahydrofuran, or their mixtures; hydrocarbons such as, for example, toluene, xylene, or their mixtures; dipolar aprotic solvents such as, for example, N,N-dimethylformamide, N-methylpyrrolidone, dimethylsulfoxide, or their mixtures; preferably 1,4-dioxane. In the said step (b), the said organic solvent can also be used in a mixture with at least one alcool such as, for example, methanol, ethanol, n-propanol, iso-propanol, or their mixtures. In accordance with a preferred embodiment of the present invention the said disubstituted halogenated diaryloxybenzoheterodiazole compound of general formula (IV) can be used in the said organic solvent in quantities such as to have a molar concentration in the said organic solvent ranging from 0.01 M to 2 M, preferably ranging from 0.02 M to 1 M.

In accordance with one preferred embodiment of the present invention the said step (b) can be carried out at a temperature ranging from 50° C. to 140° C., preferably ranging from 60° C. to 120° C.

In accordance with one preferred embodiment of the present invention the said step (b) can be carried out in a time ranging from 2 hours to 36 hours, preferably ranging from 4 hours to 18 hours.

Generally, at the end of the said process the mixture obtained, after the addition of distilled water, is extracted with an organic solvent (for example, dichloromethane) obtaining an organic phase which is washed to neutral (for example, with distilled water) and dried (for example, over sodium sulfate). Subsequently, the residual solvent is removed (for example, by distillation at reduced pressure) and the residue obtained is purified by means of normal laboratory techniques (for example, elution on a chromatography column and/or cristallisation, working as described above).

The fluorinated disubstituted benzoheterodiazole compounds of general formula (II) can be obtained in accordance with processes known in the art as described, for example, by Kularatne R. S. et al. in "*Journal of Materials Chemistry A*" (2013), Vol. 1(48), pg. 15535-15543, or by Wang N. et al. in "*Journal of the American Chemical Society*" (2013), Vol. 135(45), pg. 17060-17068, or by Zhou H. et al. in "*Angewandte Chemie International Edition*" (2011), Vol. 50(13), pg. 2995-2998, or are commercially available (in particular in the case in which $R_2=R_3$=hydrogen).

The disubstituted diaryloxybenzoheterodiazole compounds of general formula (Ia1) can be obtained in accordance with the first process which is the object of the present invention described above.

The aryl alcohols of general formula (III), the N-haloimides, the aryl-boron compounds of general formula (V) and the aryl-stannyl compounds of general formula (VI), are commercially available.

As described above, the said disubstituted diaryloxybenzoheterodiazole compound of general formula (I) can advantageously be used as a spectrum converter in luminescent solar concentrators (LSCs) which are in turn capable of improving the performance of photovoltaic devices (or solar devices) such as, for example, photovoltaic cells (or solar cells), photovoltaic modules (or solar modules), on either a rigid substrate or a flexible substrate.

The said luminescent solar concentrators (LSCs) can be prepared, for example, by dispersion in the molten state of the said disubstituted diaryloxybenzoheterodiazole compound of general formula (I) in polymer materials such as, for example, polymethylmethacrylate (PMMA), polystyrene (PS), or polyvinylacetate (PVA).

As a consequence a further object of the present invention is a luminescent solar concentrator (LSC) including at least one disubstituted diaryloxybenzoheterodiazole compound of general formula (I).

The disubstituted diaryloxybenzoheterodiazole compound of general formula (I) can be used in the said luminescent solar concentrator (LSC) in the following forms: dispersed in the polymer or in glass, chemically bound to the polymer or glass, in solution, or in the form of gel.

For example, the luminescent solar concentrator (LSC) can contain a transparent matrix, in which by the term transparent matrix is meant any transparent material used in the form of a support, binder or material in which at least one diaryloxybenzoheterodiazole compound of general formula (I) is dispersed or incorporated. The material used for the matrix is transparent, as such, to the radiation of interest and in particular to radiation having frequencies within the effective spectrum of the photovoltaic device (or solar device) such as, for example, the photovoltaic cell (or solar cell) in which it is used. Suitable materials for the purpose of the present invention can therefore be selected from materials which are transparent at least to radiations having a wavelength ranging from 250 nm to 1100 nm.

The transparent matrix which can be used for the purpose of the present invention can, for example, be selected from polymer materials or vitreous materials. The said matrix is characterised by high transparency and high durability in relation to heat and light. Polymer materials which can advantageously be used for the purpose of the present invention are, for example, polymethylmethacrylate (PMMA), epoxy resins, silicone resins, polyalkylene terephthalates, polycarbonates, polystyrene, polypropylene. Vitreous materials which can advantageously be used for the purpose of the present invention are, for example, silicas.

In the case where the matrix is of the polymer type, the said at least one disubstituted diaryloxybenzoheterodiazole compound of general formula (I) can be dispersed in the polymer of the said matrix by, for example, dispersion in the molten state, with the subsequent formation of a sheet comprising the said polymer and the said at least one disubstituted benzoheterodiazole compound of general formula (I), operating, for example, according to the technique known as "casting". Alternatively, the said at least one disubstituted diaryloxybenzoheterodiazole compound of general formula (I) and the polymer of said matrix can be dissolved in at least one solvent, obtaining a solution which is deposited on a sheet of the said polymer forming a film comprising the said at least one disubstituted diaryloxybenzoheterodiazole compound of general formula (I) and the said polymer, operating, for example, with the use of a "Doctor Blade" type film applicator: the said solvent is then allowed to evaporate.

In the case in which the matrix is of the vitreous type, the said at least one disubstituted diaryloxybenzoheterodiazole compound of general formula (I) can be dissolved in at least one solvent, obtaining a solution which is deposited on a sheet of the said matrix of vitreous type forming a film comprising the said at least one disubstituted diaryloxybenzoheterodiazole compound of general formula (I), operating, for example, with the use of a "Doctor Blade" type film applicator: the said solvent is then allowed to evaporate.

Yet another object of the present invention is a photovoltaic device (or solar device) comprising at least one photovoltaic cell (or solar cell) and at least one luminescent solar concentrator (LSC) including at least one disubstituted diaryloxybenzoheterodiazole compound of general formula (I).

The said photovoltaic device (or solar device) can, for example, be obtained by assembling the aforesaid luminescent solar concentrator with a photovoltaic cell (or solar cell).

In accordance with a preferred embodiment of the present invention the aforesaid luminescent solar concentrator (LSC) can be made in the form of a transparent sheet obtained by dissolving the said at least one disubstituted diaryloxybenzoheterodiazole compound of general formula (I) and the polymer of the matrix of the polymer type in at least one solvent, obtaining a solution which is deposited on a sheet of the said polymer forming a film comprising the said at least one disubstituted diaryloxybenzoheterodiazole compound of general formula (I) and the said polymer, operating, for example, with the use of a "Doctor Blade" type film applicator: the said solvent is then allowed to evaporate. In the said photovoltaic devices (or solar devices) the said sheets, can then be coupled with a photovoltaic cell (or solar cell).

In accordance with a further preferred embodiment of the present invention, the aforemesaid luminescent solar concentrator (LSC) can be realized in the form of a transparent sheet obtained according to the technique called casting by mixing at least one polymerizable monomer [for example, methylmethacrylate (MMA)] and at least one radical initiator [for example, azo-bis-iso-butyronitrile (AIBN)] obtaining a syrup of the pre-polymerized polymer of the matrix of the polymer type. To said syrup a solution is then added comprising at least one different radical initiator (for example, lauroyl peroxide), at least one polymerizable monomer, preferably the same monomer used to obtain the syrup, and the benzoheterodiazole compound of general formula (I), obtaining a solution that is poured into a mold of suitable dimensions and polymerized: at the end of the polymerization, the sheet obtained is removed from the mold. In said photovoltaic devices (or solar devices), the sheet thus obtained can then be coupled to a photovoltaic cell (or solar cell).

For the purpose of a better understanding of the present invention and for its implementation, a number of illustrative and non-limiting examples thereof are illustrated below.

The 4,7-di-(thien-2'-yl)-2,1,3-benzothiadiazole (DTB) was obtained as described in Example 1 of International Patent Application WO 2012/007834 in the name of the Applicant, the contents of which are incorporated here as a reference.

Example 1

Figure 1:
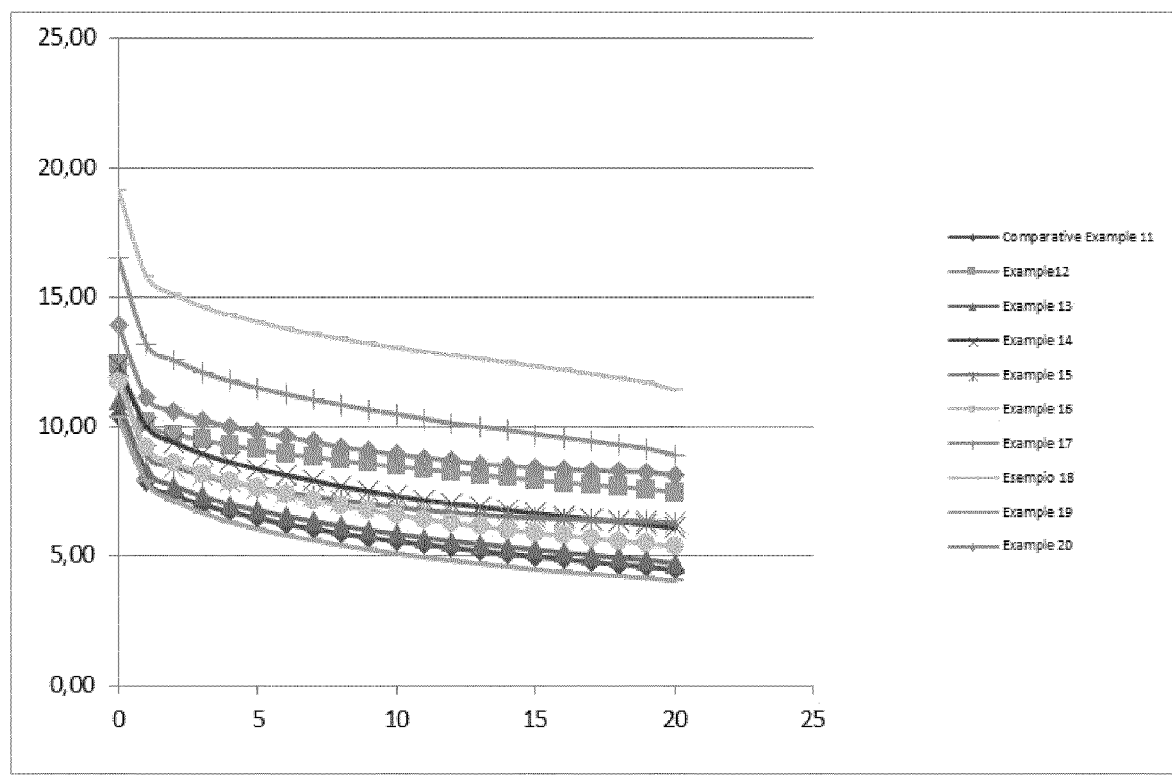
FIG. 1 shows a graph for power (P) generated, expressed in mW (shown in the ordinate), as a function of distance (d) from an edge to which a photovoltaic cell of an example or comparative example was attached, expressed in cm (shown in the abscissa).

Synthesis of 5,6-diphenoxy-4,7-bis(2-thienyl)-2,1,3-benzothiadiazole of Formula (Ia)

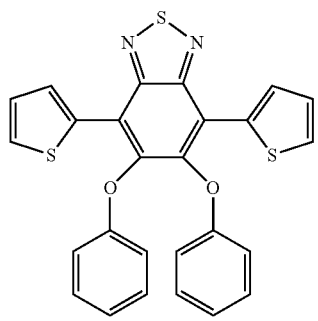

(Ia)

In a 100 ml flask, fitted with a magnetic stirrer, thermometer and condenser, in inert atmosphere, phenol (Aldrich) (742 mg; 7.9 mmoles) and potassium carbonate (Aldrich) (700 mg; 5.1 mmoles) were added to a suspension of 5,6-difluoro-4,7-bis(2-thienyl)-2,1,3-benzothiadiazole (Sunatech) (630 mg; 1.9 mmoles) in N,N-dimethylformamide (Aldrich) (6 ml): the reaction mixture obtained was heated to 92° C. and held at that temperature, with stirring, for 12 hours. Subsequently, after 20 ml of distilled water had been added, there was obtained a precipitate which was recovered by filtration and washed with distilled water (30 ml), obtaining 865 mg of 5,6-diphenoxy-4,7-bis(2-thienyl)-2,1,3-benzothiadiazole of formula (Ia) [DTB(OPh)₂] (yield=94%).

Example 2

Synthesis of 5,6-di(4-t-butylphenoxy)-4,7-bis(2-thienyl)-2,1,3-benzothiadiazole of Formula (Ib)

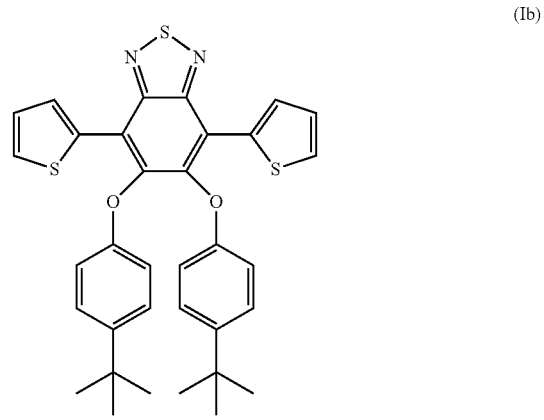 [SMILES: CC(C)(C)c1ccc(Oc2c(Oc3ccc(C(C)(C)C)cc3)c(-c3cccs3)c3nsnc3c2-c2cccs2)cc1]

(Ib)

In a 100 ml flask, fitted with a magnetic stirrer, thermometer and condenser, in inert atmosphere, 4-t-butylphenol (Aldrich) (1.2 g; 7.9 mmoles) and potassium carbonate (Aldrich) (700 mg; 5.1 mmoles) were added to a suspension of 5,6-difluoro-4,7-bis(2-thienyl)-2,1,3-benzothiadiazole (Sunatech) (630 mg; 1.9 mmoles) in N,N-dimethylformamide (Aldrich) (6 ml): the reaction mixture obtained was heated to 92° C. and held at that temperature, with stirring, for 12 hours. Subsequently, after 20 ml of distilled water had been added, there was obtained a precipitate which was recovered by filtration, washed with distilled water (30 ml), and purified by elution in a silica gel chromatography column [eluent: mixture of n-heptane (Aldrich)/ethyl acetate (Aldrich) in a ratio of 9/1 (v/v)], obtaining 1 g of 5,6-di(4-t-butylphenoxy)-4,7-bis(2-thienyl)-2,1,3-benzothiadiazole of formula (Ib) [DTB(OPhBu$^r$)₂] (yield=88%).

Example 3

Synthesis of 5,6-di(2-naphthoxy)-4,7-bis(2-thienyl)-2,1,3-benzothiadiazole of Formula (Ic)

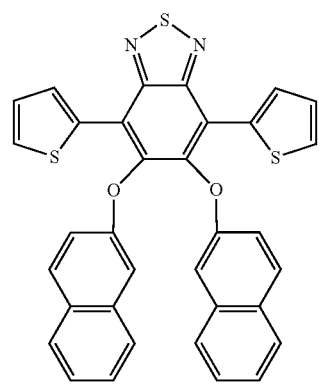

(Ic)

In a 100 ml flask, fitted with a magnetic stirrer, thermometer and condenser, in inert atmosphere, 2-naphthol (Aldrich) (300 mg; 2.08 mmoles) and potassium carbonate (Aldrich) (290 mg; 2.1 mmoles) were added to a suspension of 5,6-difluoro-4,7-bis(2-thienyl)-2,1,3-benzothiadiazole (Sunatech) (160 mg; 0.48 mmoles) in N,N-dimethylformamide (Aldrich) (2 ml): the reaction mixture obtained was heated to 92° C. and held at that temperature, with stirring, for 12 hours. Subsequently, after 10 ml of distilled water had been added, there was obtained a precipitate which was recovered by filtration, washed with distilled water (15 ml), and purified by elution in a silica gel chromatography column [eluent: mixture of n-heptane (Aldrich)/ethyl acetate (Aldrich) in a ratio of 85/15 (v/v)], obtaining 220 mg of 5,6-di(2-naphthoxy)-4,7-bis(2-thienyl)-2,1,3-benzothiadiazole of formula (Ic) [DTB(O-2-Naph)$_2$] (yield=75%).

Example 4

Synthesis of 5,6-di(4-phenylphenoxy)-4,7-bis(2-thienyl)-2,1,3-benzothiadiazole of Formula (Id)

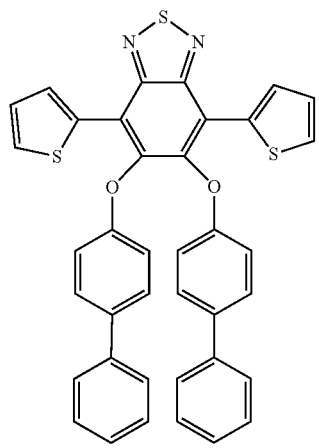

(Id)

In a 100 ml flask, fitted with a magnetic stirrer, thermometer and condenser, in inert atmosphere, 4-phenylphenol (Aldrich) (300 mg; 2.08 mmoles) and potassium carbonate (Aldrich) (290 mg; 2.1 mmoles) were added to a suspension of 5,6-difluoro-4,7-bis(2-thienyl)-2,1,3-benzothiadiazole (Sunatech) (160 mg; 0.48 mmoles) in N,N-dimethylformamide (Aldrich) (2 ml): the reaction mixture obtained was heated to 92° C. and held at that temperature, with stirring, for 12 hours. Subsequently, after 10 ml of distilled water had been added, there was obtained a precipitate which was recovered by filtration, washed with distilled water (15 ml), and purified by elution in a silica gel chromatography column [eluent: mixture of n-heptane (Aldrich)/dichloromethane (Aldrich) in a ratio of 95/5 (v/v)], obtaining 230 mg of 5,6-di(4-phenylphenoxy)-4,7-bis(2-thienyl)-2,1,3-benzothiadiazole of formula (Id) [DTB(OBPh)$_2$] (yield=75%).

Example 5

Synthesis of 5,6-di(2,6-dimethylphenoxy)-4,7-bis(2-thienyl)-2,1,3-benzothiadiazole of Formula (Ie)

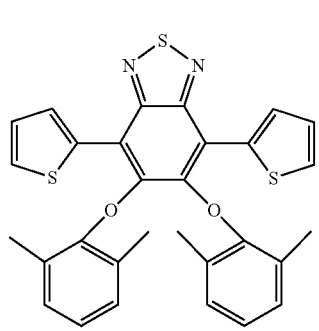

(Ie)

In a 100 ml flask, fitted with a magnetic stirrer, thermometer and condenser, in inert atmosphere, 2,6-dimethylphenol (Aldrich) (253 mg; 2.08 mmoles) and potassium carbonate (Aldrich) (290 mg; 2.1 mmoles) were added to a suspension of 5,6-difluoro-4,7-bis(2-thienyl)-2,1,3-benzothiadiazole (Sunatech) (160 mg; 0.48 mmoles) in N,N-dimethylformamide (Aldrich) (2 ml): the reaction mixture obtained was heated to 92° C. and held at that temperature, with stirring, for 12 hours. Subsequently, after 20 ml of distilled water had been added, there was obtained a precipitate which was recovered by filtration, washed with distilled water (15 ml), and purified by elution in a silica gel chromatography column [eluent: mixture of n-heptane (Aldrich)/dichloromethane (Aldrich) in a ratio of 85/15 (v/v)], obtaining 230 mg of 5,6-di(2,6-dimethylphenoxy)-4,7-bis(2-thienyl)-2,1,3-benzothiadiazole of formula (Ie) [DTB(OPh-2,6-Me$_2$)$_2$] (yield=81%).

Example 6

Synthesis of 5,6-diphenoxy-4,7-bis(5-bromo-2-thienyl)-2,1,3-benzothiadiazole of Formula (a)

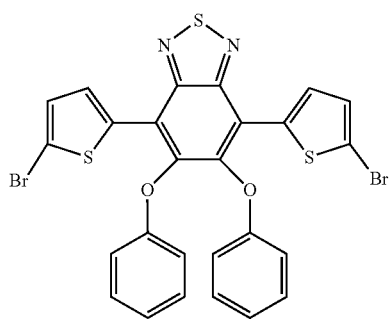

(a)

In a 100 ml flask, fitted with a magnetic stirrer, thermometer and condenser, in inert atmosphere, N-bromosuccinimide (Aldrich) (665.3 mg; 3.8 mmoles) was added to a suspension of 5,6-diphenoxy-4,7-bis(2-thienyl)-2,1,3-benzothiadiazole of formula (Ia) obtained as described in Example 1 (865 mg; 1.8 mmoles) in tetrahydrofuran (Aldrich) (10 ml): the reaction mixture obtained was left in the dark, with stirring, at ambient temperature (25° C.), for 12 hours. Subsequently, after 20 ml of distilled water had been added, there was obtained a precipitate which was recovered by filtration and washed with distilled water (30 ml), obtaining 1 g of 5,6-diphenoxy-4,7-bis(5-bromo-2-thienyl)-2,1,3-benzothiadiazole of formula (a) (yield=90%).

Example 7

Synthesis of 5,6-diphenoxy-4,7-bis[5-(2,6-dimethylphenyl)-2-thienyl]benzo[c]1,2,5-thiadiazole of Formula (If)

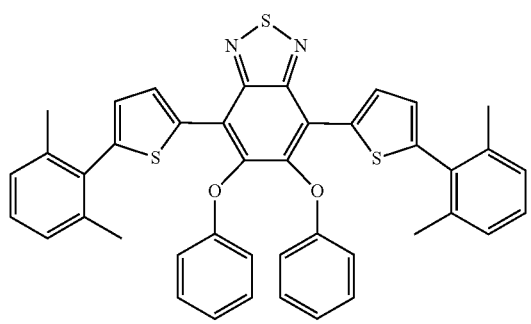

(If)

In a 100 ml flask, fitted with a magnetic stirrer, thermometer and condenser, in inert atmosphere, 2,6-dimethylphenylboronic acid (Aldrich) (158 mg; 1.05 mmoles) and an aqueous solution of 2.17 M of potassium carbonate (Aldrich) (480 mg in 1.6 ml of water; 3.47 mmoles) were added to a solution of 5,6-diphenoxy-4,7-bis(5-bromo-2-thienyl)-2,1,3-benzothiadiazole of formula (a) obtained as described in Example 6 (270 mg; 0.4 mmoles) in 1,4-dioxane (Aldrich) (5 ml). After having removed the air present by means of 3 vacuum/nitrogen cycles, palladium-tetrakistriphenylphosphine (Aldrich) (22 mg; 0.02 mmoles) was added, obtaining a reaction mixture which was heated to 95° C. and held at the said temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml), and then dried over sodium sulfate (Aldrich). The residual solvent was removed by distillation at reduced pressure. The residue obtained was purified by elution in a silica gel chromatography column [eluent: mixture of n-heptane (Aldrich)/dichloromethane (Aldrich) in a ratio of 9/1 (v/v)], obtaining 250 mg of 5,6-diphenoxy-4,7-bis[5-(2,6-dimethylphenyl)-2-thienyl]benzo[c]1,2,5-thiadiazole of formula (If) [5-(2,6-Me$_2$Ph)$_2$DTB(OPh)$_2$] (yield=90%).

Example 8

Synthesis of 5,6-diphenoxy-4,7-bis[5-(2,5-dimethylphenyl)-2-thienyl]benzo[c]1,2,5-thiadiazole of Formula (Ig)

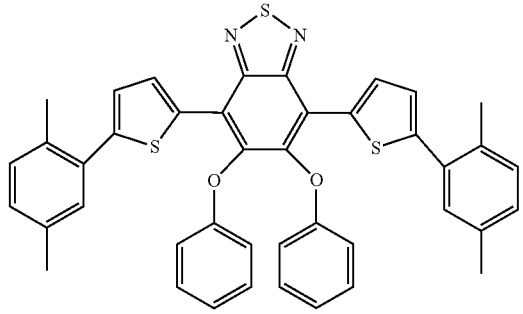

(Ig)

In a 100 ml flask, fitted with a magnetic stirrer, thermometer and condenser, in inert atmosphere, 2,5-dimethylphenylboronic acid (Aldrich) (158 mg; 1.05 mmoles) and an aqueous solution of 2.17 M of potassium carbonate (Aldrich) (480 mg in 1.6 ml of water; 3.47 mmoles) were added to a solution of 5,6-diphenoxy-4,7-bis(5-bromo-2-thienyl)-2,1,3-benzothiadiazole of formula (a) obtained as described in Example 6 (270 mg; 0.4 mmoles) in 1,4-dioxane (Aldrich) (5 ml). After having removed the air present by means of 3 vacuum/nitrogen cycles, palladium-tetrakistriphenylphosphine (Aldrich) (22 mg; 0.02 mmoles) was added, obtaining a reaction mixture which was heated to 95° C. and held at the said temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and then dried over sodium sulfate (Aldrich). The residual solvent was removed by distillation at reduced pressure. The residue obtained was purified by elution in a silica gel chromatography column [eluent: mixture of n-heptane (Aldrich)/dichloromethane (Aldrich) in a ratio of 9/1 (v/v)], obtaining 250 mg of 5,6-diphenoxy-4,7-bis[5-(2,5-dimethylphenyl)-2-thienyl]benzo[c]1,2,5-thiadiazole of formula (Ig) [5-(2,5-Me$_2$Ph)$_2$DTB(OPh)$_2$] (yield=90%).

Example 9

Synthesis of 5,6-diphenoxy-4,7-bis[5-(2,6-di-iso-propylphenyl)-2-thienyl]benzo[c]1,2,5-thiadiazole of Formula (Ih)

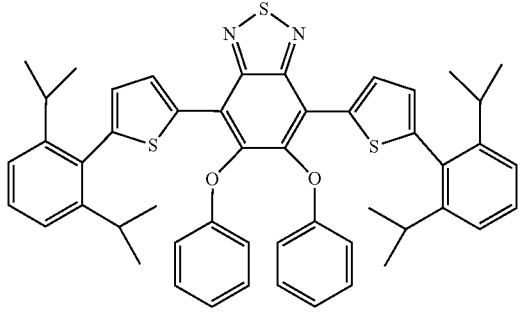

(Ih)

In a 100 ml flask, fitted with a magnetic stirrer, thermometer and condenser, in inert atmosphere, 2,6-di-iso-propylphenylboronic acid (Aldrich) (387 mg; 1.8 mmoles) and caesium carbonate (Aldrich) (940 mg; 2.88 mmoles) were added to a solution of 5,6-diphenoxy-4,7-bis(5-bromo-2-thienyl)-2,1,3-benzothiadiazole of formula (a) obtained as described in Example 6 (300 mg; 0.47 mmoles) in 1,4-dioxane (Aldrich) (5 ml). After having removed the air present by means of 3 vacuum/nitrogen cycles, bis-triphenylphosphine palladium dichloride (Aldrich) (34 mg; 0,048 mmoles) was added obtaining a reaction mixture which was heated to 85° C. and held at the said temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml), and then dried over sodium sulfate (Aldrich). The residual solvent was removed by distillation at reduced pressure. The residue obtained was purified by elution in a silica gel chromatography column [eluent: mixture of n-heptane (Aldrich)/dichloromethane (Aldrich) in a ratio of 9/1 (v/v)], obtaining 270 mg of 5,6-diphenoxy-4,7-bis[5-(2,6-di-iso-propylphenyl)-2-thienyl]benzo[c]1,2,5-thiadiazole of formula (Ih) [5-(2,6-Pr$^i_2$Ph)$_2$DTB(OPh)$_2$] (yield=71%).

Example 10

Synthesis of 5,6-diphenoxy-4,7-bis[5-(2-naphthyl)-2-thienyl]benzo[c]1,2,5-thiadiazole of Formula (Ii)

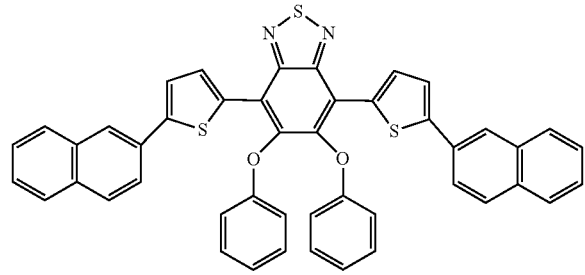

(Ii)

In a 100 ml flask, fitted with a magnetic stirrer, thermometer and condenser, in inert atmosphere, 2-naphthylboronic acid (Aldrich) (178 mg; 1.03 mmoles) and an aqueous solution of 2.1 M of potassium carbonate (Aldrich) (419 mg in 1.44 ml of water; 3.04 mmoles) were added to a solution of 5,6-diphenoxy-4,7-bis(5-bromo-2-thienyl)-2,1,3-benzothiadiazole of formula (a) obtained as described in Example 6 (245.8 mg; 0.38 mmoles) in 1,4-dioxane (Aldrich) (15 ml). After having removed the air present by means of 3 vacuum/nitrogen cycles, palladium-tetrakistriphenylphosphine (Aldrich) (22 mg; 0.02 mmoles) (Aldrich) was added, obtaining a reaction mixture which was heated to 95° C. and held at the said temperature, with stirring, for 14 hours. The reaction mixture was then poured into distilled water (50 ml) and extracted with dichloromethane (Aldrich) (3×25 ml). The organic phase obtained was washed to neutral with distilled water (3×25 ml) and then dried over sodium sulfate (Aldrich). The residual solvent was removed by distillation at reduced pressure. The residue obtained was purified by elution in a silica gel chromatography column [eluent: mixture of n-heptane (Aldrich)/ethyl acetate (Aldrich) in a ratio of 85/15 (v/v)], obtaining 250 mg of 5,6-diphenoxy-4,7-bis[5-(2-naphthyl)-2-thienyl]benzo[c]1,2,5-thiadiazole of formula (Ii) [5-(2-Naph)$_2$DTB(OPh)$_2$] (yield=89%).

Example 11 (Comparative)

6 g of Altuglas VSUVT 100 (PMMA) polymethylmethacrylate and 49.5 mg of 4,7-di-(thien-2'-yl)-2,1,3-benzothiadiazole (DTB), were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of a yellow colour imparted by the film, whose thickness was ranging from 100 μm to 50 μm.

An IXYS-KXOB22-12 photovoltaic cell having a surface area of 1.2 cm$^2$ was then applied to one of the edges of the polymer sheet The main surface of the polymer sheet [that coated with the thin film containing the 4,7-di-(thien-2'-yl)-2,1,3-benzothiadiazole (DTB)] was then illuminated with a light source having a power of 1 sun (1000 W/m$^2$) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge and auto absorption effects.

It will be seen how in the absence of edge effects the mean power generated was 5.69 mW (FIG. 1).

Figure 2:
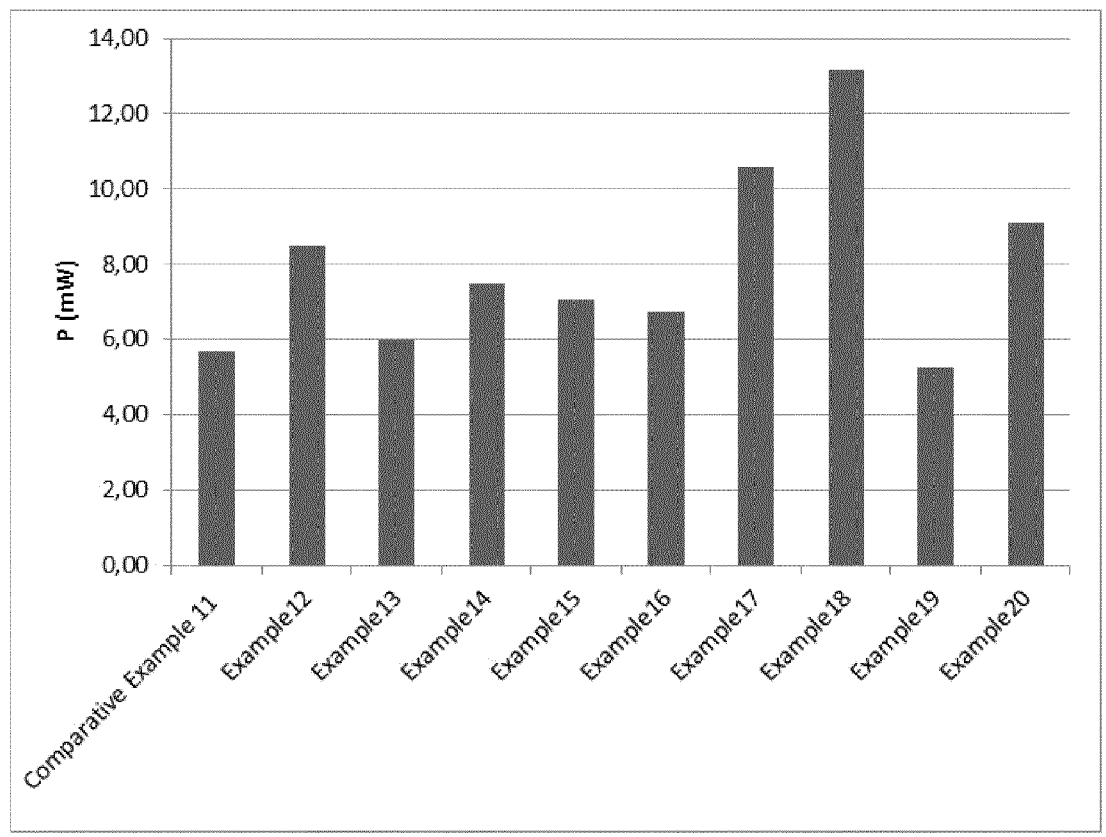
FIG. 2 shows an obtained value of power (P) generated, expressed in mW (shown in the ordinate) (the number of an example or comparative example is shown in the abscissa).

FIG. 2 shows the obtained value of the power (P) generated, expressed in mW (shown in the ordinate), (the number of the example is shown in the abscissa).

Example 12

6 g of Altuglas VSUVT 100 (PMMA) polymethylmethacrylate and 87.1 mg of 5,6-diphenoxy-4,7-bis(2-thienyl)-2,1,3-benzothiadiazole of formula (Ia) [DTB(OPh)$_2$] obtained as described in Example 1, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of a red colour imparted by the film, whose thickness was ranging from 100 µm to 50 µm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source having a power of 1 sun (1000 W/m²) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects.

It will be seen how in the absence of edge effects the mean power generated was 8.49 mW (FIG. 1).

FIG. 2 shows the obtained value of the power (P) generated, expressed in mW (shown in the ordinate), (the number of the example is shown in the abscissa).

Example 13

6 g of Altuglas VSUVT 100 (PMMA) polymethylmethacrylate and 105 mg of 5,6-di(4-t-butylphenoxy)-4,7-bis(2-thienyl)-2,1,3-benzothiadiazole of formula (Ib) [DTB(OPh-Bu)$_2$] obtained as described in Example 2 were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 µm to 50 µm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source having a power of 1 sun (1000 W/m²) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 5.98 mW (FIG. 1).

FIG. 2 shows the obtained value of the power (P) generated, expressed in mW (shown in the ordinate), (the number of the example is shown in the abscissa).

Example 14

6 g of Altuglas VSUVT 100 (PMMA) polymethylmethacrylate and 105.2 mg of 5,6-di(2-naphthoxy)-4,7-bis(2-thienyl)-2,1,3-benzothiadiazole of formula (Ic) [DTB(O-2-Naph)$_2$] obtained as described in Example 3, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 µm to 50 µm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source having a power of 1 sun (1000 W/m²) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 7.48 mW (FIG. 1).

FIG. 2 shows the obtained value of the power (P) generated, expressed in mW (shown in the ordinate), (the number of the example is shown in the abscissa).

Example 15

6 g of Altuglas VSUVT 100 (PMMA) polymethylmethacrylate and 82.6 mg of 5,6-di(4-phenylphenoxy)-4,7-bis(2-thienyl)-2,1,3-benzothiadiazole of formula (Id) [DTB(OBPh)$_2$] obtained as described in Example 4, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 µm to 50 µm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source having a power of 1 sun (1000 W/m²) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 7.06 mW (FIG. 1).

FIG. 2 shows the obtained value of the power (P) generated, expressed in mW (shown in the ordinate), (the number of the example is shown in the abscissa).

Example 16

6 g of Altuglas VSUVT 100 (PMMA) polymethylmethacrylate and 97.2 mg of 5,6-di(2,6-dimethylphenoxy)-4,7-bis(2-thienyl)-2,1,3-benzothiadiazole of formula (Ie) [DTB(OPh-2,6-Me$_2$)$_2$] obtained as described in Example 5, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 μm to 50 μm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source having a power of 1 sun (1000 W/m$^2$) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 6.73 mW (FIG. 1).

FIG. 2 shows the obtained value of the power (P) generated, expressed in mW (shown in the ordinate), (the number of the example is shown in the abscissa).

Example 17

6 g of Altuglas VSUVT 100 (PMMA) polymethylmethacrylate and 124.6 mg of 5,6-diphenoxy-4,7-bis[5-(2,6-dimethylphenyl)-2-thienyl]benzo[c]1,2,5-thiadiazole of formula (If) [5-(2,6-Me$_2$Ph)$_2$DTB(OPh)$_2$] obtained as described in Example 7, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 μm to 50 μm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source having a power of 1 sun (1000 W/m$^2$) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects.

It will be seen how in the absence of edge effects the mean power generated was 10.58 mW (FIG. 1).

FIG. 2 shows the obtained value of the power (P) generated, expressed in mW (shown in the ordinate), (the number of the example is shown in the abscissa).

Example 18

6 g of Altuglas VSUVT 100 (PMMA) polymethylmethacrylate and 124.6 mg of 5,6-diphenoxy-4,7-bis[5-(2,5-dimethylphenyl)-2-thienyl]benzo[c]1,2,5-thiadiazole of formula (Ig) [5-(2,5-Me$_2$Ph)$_2$DTB(OPh)$_2$] obtained as described in Example 8, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 μm to 50 μm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source having a power of 1 sun (1000 W/m$^2$) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 13.17 mW (FIG. 1).

FIG. 2 shows the obtained value of the power (P) generated, expressed in mW (shown in the ordinate), (the number of the example is shown in the abscissa).

Example 19

6 g of Altuglas VSUVT 100 (PMMA) polymethylmethacrylate and 144.7 mg of 5,6-diphenoxy-4,7-bis[5-(2,6-di-iso-propylphenyl)-2-thienyl]benzo[c]1,2,5-thiadiazole of formula (Ih) [5-(2,6-Pr$^i_2$Ph)$_2$DTB(OPh)$_2$] obtained as described in Example 9, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 μm to 50 μm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source having a power of 1 sun (1000 W/m$^2$) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 5.28 mW (FIG. 1).

FIG. 2 shows the value of the power (P) generated, expressed in mW (shown in the ordinate), (the number of the example is shown in the abscissa).

Example 20

6 g of Altuglas VSUVT 100 (PMMA) polymethylmethacrylate and 49.5 mg of 5,6-diphenoxy-4,7-bis[5-(2-naphthyl)-2-thienyl]benzo[c]1,2,5-thiadiazole of formula (Ii) [5-(2-Naph)$_2$DTB(OPh)$_2$] obtained as described in Example 10, were dissolved in 30 ml of 1,2-dichlorobenzene (Aldrich). The solution obtained was then deposited uniformly on a sheet of polymethylmethacrylate (dimensions 300 mm×90 mm×6 mm) using a "Doctor Blade" type film applicator and the solvent was allowed to evaporate at ambient temperature (25° C.), in a gentle flow of air, for 24 hours. This yielded a transparent sheet of an orange colour imparted by the film, whose thickness was ranging from 100 μm to 50 μm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source having a power of 1 sun (1000 W/m$^2$) and the electrical power generated by the illumination was then measured.

Power (P) was then measured by illuminating one portion of sheet of dimensions 100 mm×90 mm at an increasing distance (d) from the edge to which the photovoltaic cell was attached. These measurements at a variable distance from the photovoltaic cell help to quantify the contributions of wave guide, edge, diffusion and auto absorption effects. It will be seen how in the absence of edge effects the mean power generated was 9.09 mW (FIG. 1).

FIG. 2 shows the obtained value of the power (P) generated, expressed in mW (shown in the ordinate), (the number of the example is shown in the abscissa).

Example 21 (Comparative) 22-24 (Invention)

400 ml of methyl methacrylate (MMA) (Aldrich 99%), previously distilled, were heated to 80° C., in 2 hours, under magnetic agitation, in a 1 liter flask.

Subsequently, 40 mg of azo-bis-iso-butyronitrile (AIBN) (Aldrich 98%) dissolved in 40 ml of methyl methacrylate (MMA) (Aldrich 99%), previously distilled, were added: the mixture obtained was heated, under magnetic agitation, to 94° C., in 1 hour, left at said temperature for 2 minutes, and subsequently cooled in an ice bath, obtaining a syrup of pre-polymerized polymethyl-methacrylate (PMMA). 400 ml of the pre-polymerized syrup obtained as described above were loaded into a 1 liter flask, and 25 mg of lauroyl peroxide (Acros 99%) dissolved in methyl methacrylate (MMA) (Aldrich 99%), previously distilled, were added, and a quantity of 4,7-di(thien-2'-il)-2,1,3-benzothiadiazole (DTB) [in Example 21 (comparative)] or of disubstituted diaryloxybenzoheterodiazole compound of general formula (I), obtained as described in the examples reported above [in Examples 22 (invention): compound (Ia) of Example 1; in Example 23 (invention): compound (If) of Example 7; and in Example 24 (invention): compound (Ig) of Example 8], such that the molar percentage of said 4,7-di(thien-2'-il)-2,1,3-benzothiadiazole (DTB) or of said disubstituted diaryloxybenzoheterodiazole compound of general formula (I), with respect to methyl methacrylate (MMA) is equal to 0.3. The mixture obtained was degassed, under magnetic agitation, under a vacuum of 10 mm mercury (Hg), for 45 minutes, at ambient temperature (25° C.), obtaining a solution that was poured into the mold described below.

Said mold was formed by two sheets of glass with dimensions 40×40 cm and thickness 6 mm-10 mm, separated by polyvinylchloride (PVC) gaskets (10 cm diameter). Said sheets of glass were mounted between jaws and pressed together until the space between the two sheets was about 6 mm. After closing the opening through which the aforementioned solution was poured with the gasket, the mold was immersed in a water bath, at 55° C., for 48 hours, and then placed in the stove and heated to 95° C. for 24 hours. Subsequently, the mold was cooled to ambient temperature (25° C.), the jaws and the gasket were removed, the glass sheets of the mold were separated, and the sheet of polymethylmethacrylate (PMMA) obtained was collected. The sheet of polymethyl-methacrylate (PMMA) was then cut into sheets with dimensions 30×7.5 cm in order to carry out the aging tests reported below.

The different sheets obtained as described above were subjected to accelerated aging in an ATLAS XenoTest Beta+, equipped with a Xenon lamp cooled in air and with Xenochrome 300 filter, operating in accordance with standard DIN EN ISO 4892-2-A1 2003-11.

Periodically, the sheets were removed and subjected to UV-visible spectroscopy. The ultraviolet and visible absorption spectra (190 nm-850 nm) were recorded with a double beam UV-Vis-NIR spectrophotometer and double monochromator, with a passband of 2.0 nm and step of 1 nm.

Therefore, through said UV-visible spectroscopy, the quantity of fluorescent compound present on the sheets was determined by measuring the characteristic absorbance of each fluorescent compound, subject to calibration through reference sheets containing known quantities of fluorescent compound dispersed in the polymeric matrix itself.

In the sheets subject to accelerated aging the spectrophotometry of UV-vis absorption allowed the absorbance reduction in the visible region to be monitored by measuring the relative absorbance percentage (A %) defined as (At)/(A0), i.e. the ratio of absorbance at time t (At) to absorbance at time 0 (A0): in particular, the absorbance values (At) and (A0) are the mean of the absorbance values measured on each sheet in various points, at time t and at time zero, respectively.

Table 2 reports the relative absorbance percentage values (A %) [(At)/(A0)] according to the aging time [t (h)].

TABLE 2

| | (A%) [(At)/(A0)] | | | |
|---|---|---|---|---|
| t (h) | Example 21 (DTB) | Example 22 [compound (Ia)] | Example 23 [compound (If)] | Example 24 [compound (Ig)] |
| 0 | 100 | 100 | 100 | 100 |
| 300 | 84 | 93 | 98 | 96 |
| 500 | 66 | 87 | 100 | 95 |
| 900 | — | 79 | 96 | 91 |
| 1000 | 51 | — | — | — |
| 1500 | 32 | 64 | 93 | 85 |
| 1800 | 17 | — | 92 | 82 |
| 2000 | — | — | — | — |

From the data reported in Table 2 it can be inferred that the fluorescent compounds in accordance with the present invention (Examples 22-24) have a higher relative absorbance percentage (A %) even after a number of hours of aging, with respect to 4,7-di(thien-2'-yl)-2,1,3-benzothiadiazole (DTB) known in the art [Example 21 (comparative)].

The invention claimed is:
1. Process for the preparation of a disubstituted diaryloxybenzoheterodiazole compound of general formula (I):

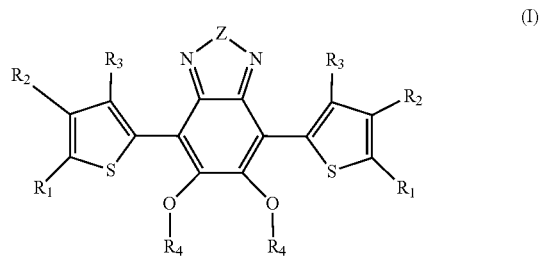

in which Z represents a sulfur atom, an oxygen atom, a selenium atom; or an $NR_5$ group in which $R_5$ is selected from linear or branched $C_1$-$C_{20}$ alkyl groups, or from optionally substituted aryl groups;

$R_1$, which are the same as each other, represent a hydrogen atom, $R_2$ and $R_3$, which are the same or different, represent a hydrogen atom; or are selected from linear or branched $C_1$-$C_{20}$ alkyl groups; linear or branched $C_1$-$C_{20}$ alkyl groups containing heteroatoms; optionally substituted cycloalkyl groups; optionally substituted aryl groups; optionally substituted linear or branched $C_1$-$C_{20}$ alkoxyl groups; optionally substituted phenoxyl groups, or —$OCOR_6$ groups in which $R_6$ is selected from linear or branched $C_1$-$C_{20}$ alkyl groups, or is a cyano group;

or $R_2$ and $R_3$ can optionally be linked together so as to form, together with the carbon atoms to which they are linked, a saturated, unsaturated or aromatic cyclic ring or a polycyclic system containing from 3 to 14 carbon atoms, optionally containing one or more heteroatoms;

$R_4$, which are the same or different, are selected from optionally substituted aryl groups, comprising reacting at least one fluorinated disubstituted benzoheterodiazole compound of formula (II):

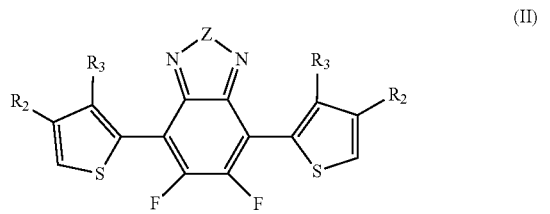

(II)

in which Z has the same meanings as described above, $R_2$ and $R_3$, have the same meanings as described above, with at least one aryl alcohol of general formula (III):

$R_4$—OH              (III)

in which $R_4$ has the same meanings as described above; said fluorinated disubstituted diarylbenzoheterodiazole compound of general formula (II) and said aryl alcohol of general formula (III) being used in molar ratios ranging from 1:2 to 1:10.

2. Process for the preparation of a disubstituted diaryloxybenzoheterodiazole compound of general formula (I) according to claim 1, wherein said process is carried out:

in a presence of at least one weak organic base selected from: carboxylates of alkali metals or of alkaline-earth metals, or their mixtures; carbonates of alkali metals or of alkaline-earth metals, or their mixtures; or bicarbonates of alkali metals or of alkaline-earth metals, or their mixtures; said fluorinated disubstituted diarylbenzoheterodiazole compound of general formula (II) and said weak organic base being used in molar ratios ranging from 1:1 to 1:10; and/or in a presence of at least one organic solvent selected from 1,2-dimethoxyethane, 1,4-dioxane, tetrahydrofuran, or their mixtures; toluene, xylene, or their mixtures; or N,N-dimethylformamide, N-methylpyrrolidone, dimethylsulfoxide; or their mixtures; said fluorinated disubstituted diarylbenzoheterodiazole compound of general formula (II) being used in said organic solvent in such a quantity as to have a molar concentration in said organic solvent ranging from 0.05 M to 2 M;

at a temperature ranging from 60° C. to 150° C., for a time ranging from 1 hour to 24 hours.

3. Process for the preparation of a disubstituted diaryloxybenzoheterodiazole compound of general formula (I):

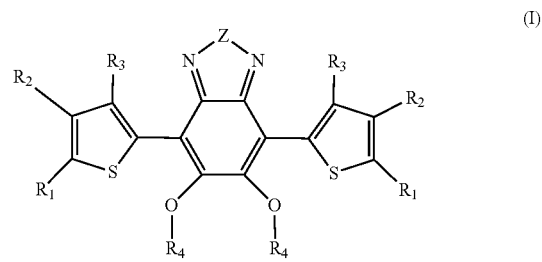

(I)

in which Z represents a sulfur atom, an oxygen atom, a selenium atom; or an $NR_5$ group in which $R_5$ is selected from linear or branched $C_1$-$C_{20}$ alkyl groups, or from optionally substituted aryl groups;

$R_1$, $R_2$ and $R_3$, which are the same or different, represent a hydrogen atom; or are selected from linear or branched $C_1$-$C_{20}$ alkyl groups; linear or branched $C_1$-$C_{20}$ alkyl groups containing heteroatoms; optionally substituted cycloalkyl groups; optionally substituted aryl groups; optionally substituted linear or branched $C_1$-$C_{20}$ alkoxyl groups; optionally substituted phenoxyl groups, or —$OCOR_6$ groups in which $R_6$ is selected from linear or branched $C_1$-$C_{20}$ alkyl groups, or is a cyano group;

wherein said optionally substituted aryl group of $R_1$ is selected from optionally substituted phenyl, naphthyl, phenyl naphthyl, phenanthrene or anthracene;

or $R_1$ and $R_2$, can optionally be linked together so as to form, together with the carbon atoms to which they are linked, a saturated, unsaturated or aromatic cyclic ring or a polycyclic system containing from 3 to 14 carbon atoms, optionally containing one or more heteroatoms;

or $R_2$ and $R_3$ can optionally be linked together so as to form, together with the carbon atoms to which they are linked, a saturated, unsaturated or aromatic cyclic ring or a polycyclic system containing from 3 to 14 carbon atoms, optionally containing one or more heteroatoms;

$R_4$, which are the same or different, are selected from optionally substituted aryl groups;

in which at least one of $R_1$, $R_2$ and $R_3$ is/are different from hydrogen, comprising the following steps:

(a) reacting at least one disubstituted diaryloxybenzoheterodiazole compound of general formula (Ia1):

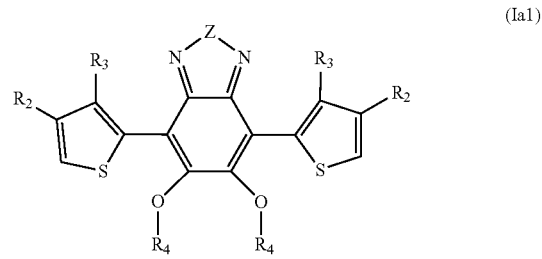

(Ia1)

in which Z, $R_2$, $R_3$ and $R_4$, have the same meanings as described above, with at least one N-haloimides compound selected from N-bromosuccinimide, N-bromophthalimide, N-iodosuccinimide, or N-iodophthalimide, obtaining a disubstituted halogenated diaryloxybenzoheterodiazole compound of general formula (IV):

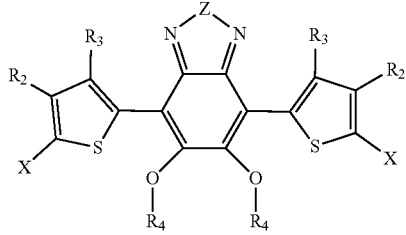

(IV)

in which Z, $R_2$, $R_3$ and $R_4$, have the same meanings as described above and X is a halogen atom selected from bromine or iodine; said disubstituted diaryloxybenzoheterodiazole compound of general formula (Ia1) and said N-haloimides compound being used in molar ratios ranging from 1:2 to 1:3;

(b) reacting the disubstituted halogenated diaryloxybenzoheterodiazole compound of general formula (IV) obtained in step (a) with:
(i) at least one aryl-boron compound of general formula (V):

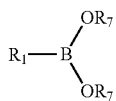

(V)

in which $R_1$ has the same meanings as described above, provided that the $R_1$ substituent does not represent a hydrogen atom, and the $R_7$ substituents represent a hydrogen atom, or can be selected from linear or branched $C_1$-$C_{10}$ alkyl groups or optionally substituted cycloalkyl groups, or the two $R_7$ substituents can optionally be linked together so as to form, together with other atoms to which they are linked, a cyclic ring selected from pinacol esters of boronic acid or 1,3-propanodiol esters of boronic acid; or
(ii) with at least one aryl-stannylated compound of general formula (VI):

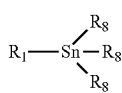

(VI)

in which $R_1$ has the same meanings as described above, provided that the $R_1$ substituent does not represent a hydrogen atom, and the $R_8$ substituents can be selected from linear or branched $C_1$-$C_8$ alkyl groups; said disubstituted halogenated diaryloxybenzoheterodiazole compound of general formula (IV) and said aryl-boron compound of general formula (V), or said aryl-stannylated compound of general formula (VI) being used in molar ratios ranging from 1:2 to 1:5.

4. Process for the preparation of a disubstituted diaryloxybenzoheterodiazole compound of general formula (I) according to claim 3, wherein said step (a) is carried out in a presence of at least one organic solvent selected from: 1,2-dimethoxyethane, 1,4-dioxane, tetrahydrofuran, or their mixtures; chlorinated solvents selected from dichloromethane, chloroform, or their mixtures; or dipolar aprotic solvents selected from N,N-dimethylformamide, N-methylpyrrolidone, dimethylsulfoxide; or their mixtures; said disubstituted diaryloxybenzoheterodiazole compound of general formula (Ia1) being used in said organic solvent in such a quantity as to have a molar concentration in said organic solvent ranging from 0.01 M to 5 M at a temperature ranging from 20° C. to 50° C. for a time ranging from 1 hour to 24 hours.

5. Process for the preparation of a disubstituted diaryloxybenzoheterodiazole compound of general formula (I) according to claim 3, wherein said step (b) is carried out:
in a presence of palladium catalyst containing at least one compound selected from palladium in oxidation state (0) or (II) selected from palladium-tetrakistriphenylphosphine [Pd(PPh$_3$)$_4$] or palladium bis-triphenylphosphine dichloride [PdCl$_2$(PPh$_3$)$_2$]; said disubstituted halogenated diaryloxybenzoheterodiazole compound of general formula (IV) and said palladium catalyst being used in molar ratios ranging from 1:0.15 to 1:0.01; and/or
in a presence of at least one weak organic base selected from: carboxylates of alkali metals or of alkaline-earth metals, or their mixtures; carbonates of alkali metals or of alkaline-earth metals, or their mixtures; or bicarbonates of alkali metals or of alkaline-earth metals, or their mixtures said disubstituted halogenated diaryloxybenzoheterodiazole compound of general formula (IV) and said weak organic base being used in molar ratios ranging from 1:1 to 1:20; and/or
in a presence of at least one organic solvent selected from: 1,2-dimethoxyethane, 1,4-dioxane, tetrahydrofuran, or their mixtures; toluene, xylene, or their mixtures; or N,N-dimethylformamide, N-methylpyrrolidone, dimethylsulfoxide, or their mixtures; or their mixtures;-optionally in admixture with at least one alcohol selected from methanol, ethanol, n-propanol, iso-propanol, or their mixtures; said disubstituted halogenated diaryloxybenzoheterodiazole compound of general formula (IV) being used in said organic solvent in such a quantity as to have a molar concentration in said organic solvent ranging from 0.01 M to 2 M;
at a temperature ranging from 50° C. to 140° C. for a time ranging from 2 hours to 36 hours.

* * * * *